United States Patent [19]

Homma et al.

[11] 4,079,126

[45] Mar. 14, 1978

[54] **METHOD OF PREPARING A COMPONENT CONSISTING OF SUGAR, LIPID AND PROTEIN DERIVED FROM *PSEUDOMONAS AERUGINOSA* WHICH POSSESS ANTI-TUMOR AND INTERFERON INDUCING PROPERTIES**

[75] Inventors: J. Yuzuru Homma, Tokyo; Chiyoji Abe, Yokohama; Kenichi Tanamoto, Tokyo; Kazuo Kuretani, Tokyo; Akio Hoshi, Tokyo, all of Japan

[73] Assignee: President of the University of Tokyo, Tokyo, Japan

[21] Appl. No.: 668,564

[22] Filed: Mar. 19, 1976

[30] Foreign Application Priority Data

May 14, 1975 Japan .................................. 50-55979

[51] Int. Cl.² ...................... A61K 39/02; C12D 13/02
[52] U.S. Cl. ........................................ 424/92; 195/96; 195/29
[58] Field of Search .............................. 195/96, 2, 4; 424/85–87, 92

[56] References Cited

U.S. PATENT DOCUMENTS

| 3,786,141 | 1/1974 | Ogawa et al. ..................... 195/96 X |
| 3,876,779 | 4/1975 | Adam et al. ........................ 195/96 X |

FOREIGN PATENT DOCUMENTS 1,365,950  9/1974  United Kingdom.

*Primary Examiner*—Lionel M. Shapiro
*Attorney, Agent, or Firm*—Blum, Moscovitz, Friedman & Kaplan

[57] ABSTRACT

This invention relates to a method of preparing original endotoxin protein of *Pseudomonas aeruginosa*. The invention relates more particularly to a method of preparing original endotoxin protein of *Pseudomonas aeruginosa* (hereunder abbreviated as OEP) by processing with either proteolytic enzyme or reductant, or further processing with proteolytic enzyme after it has been treated with reductant. The invention also relates to the original endotoxin protein derived from *Pseudomonas aeruginosa*.

18 Claims, 2 Drawing Figures

METHOD OF PREPARING A COMPONENT CONSISTING OF SUGAR, LIPID AND PROTEIN DERIVED FROM *PSEUDOMONAS AERUGINOSA* WHICH POSSESS ANTI-TUMOR AND INTERFERON INDUCING PROPERTIES

BACKGROUND OF THE INVENTION

*Pseudomonas aeruginosa* is known to be naturally resistant against most of the antibiotics in general use. Despite the fact that some few antibiotics are effective, the use of antibiotics is not effective in such cases as neonates who are physiologically immature in immune response or in cases when immunity depressant is administered. On the other hand, both adult human beings and animals possessing normal immunity could hardly be victims of natural infection by this bacterial genus, and even when infected, antibiotics are effective for them.

In view of the above, it can well be realized that immunity against this bacterial genus is effective for infection caused by the same bacillus. In fact, for a certain type of infection by this bacterial genus, either active or passive immunity (serum or plasma) is effective.

The thermostabile O antigen, a lipopolysaccharide (LPS) derived from *Pseudomonas aeruginosa* is known as an antigen originating in *Pseudomonas aeruginosa* and possessing the capability of protecting human, mouse and rabbit from infection caused by the homologous serotype strains of *Pseudomonas aeruginosa*.

However, because this O antigen is immunologically specific in its protective activity, it has the disadvantage that humans and animals immunized by a particular O antigen can be protected from infections caused only by the bacterial strains belonging to the same homologous serotype strain as the immunogen but it can hardly be protective against such infections as are due to bacterial strains whose serological specificity is heterologous.

Nevertheless, according to a method of isolating OEP from *Pseudomonas aeruginosa* disclosed in the British Pat. No. 1,365,950, and the product referred to therein as CWP in the above U.K. patent being equivalent to the OEP referred to in connection with the present invention, OEP almost completely free of O antigen can be isolated from *Pseudomonas aeruginosa*, and this OEP has been proved to be an antigen which can also protect humans, mice and rabbits from infection by different serotype strains of *Pseudomonas aeruginosa* to a great extent.

SUMMARY OF THE INVENTION

A dissociant strain of *Pseudomonas aeruginosa* was inoculated in a fermenter and cultured at 37° C. A quantity of an autolyzing agent such as toluene or chloroform was added to the bacterial culture several hours after the stationary state had been reached, so that it could be autolyzed. A component (OEP) consisting mainly of protein, and a small amount of lipid and sugar was isolated from the culture filtrate and purified by physicochemical methods until it was homogeneous. Then, the OEP thus obtained was processed by either proteolytic enzyme or reductant, or after the processing by reductant further digested by proteolytic enzymes derived from animal, plant or microorganism thereby preparing the bacterial component of *Pseudomonas aeruginosa*, possessing extremely strong anti-tumor and interferon inducing activities. This component possesses a specific preventive property against infection due to *Pseudomonas aeruginosa* and non-specific protective property against infections by *Pseudomonas aeruginosa* as well as the other bacterial strains. When immunized with the bacterial component of *Pseudomonas aeruginosa* mentioned above, an excellent preventive activity against virus and invasion of tumor cold be obtained, and this bacterial component could also prevent infections by certain serotype strains of *Pseudomonas aeruginosa*.

Accordingly, it is an object of the present invention to provide a method of obtaining OEP from *Pseudomonas aeruginosa* which is an improvement over the method disclosed in British Pat. No. 1,365,950.

Another object of the present invention is to provide a method of preparing a bacterial component of *Pseudomonas aeruginosa* possessing a more powerful biological activity (anti-tumor and interferon-inducing activities) by further processing OEP obtained according to the British Pat. No. 1,365,950 with either reductant or with proteolytic enzyme or with proteolytic enzyme after treatment with reductant.

An important object of the present invention is a bacterial component of *Pseudomonas aeruginosa* possessing anti-tumor and interferon-inducing activities.

Still other objects and advantages of the invention will in part be obvious and will in part be apparent from the specification.

The invention accordingly comprises the several steps and the relation of one or more of such steps with respect to each of the others, and the composition possessing the features, properties, and the relation of constituents which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 2:
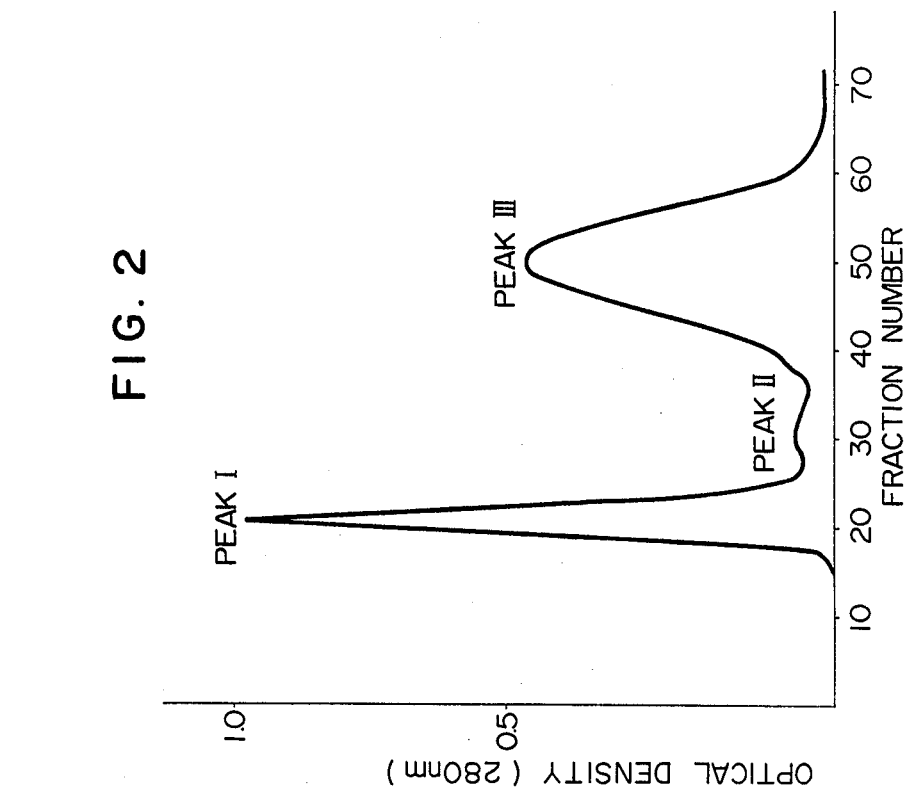
FIG. 2 is a graph showing the elution pattern of the substance of peak I in FIG. 1 treated with alkaline protease resulting from a column chromatography on Sephadex G75.

A dissociant strain of *Pseudomonas aeruginosa* was inoculated in a fermenter and cultured at 37° C. A quantity of an autolyzing agent such as toluene or chloroform was added to the bacterial culture several hours after the stationary state had been reached, so that it could be autolyzed. A component consisting mainly of protein, and a small amount of lipid and sugar (hereunder abbreviated as OEP), was isolated from the culture filtrate and purified by physicochemical methods until it was homogeneous.

Then, the OEP thus obtained was processed by either proteolytic enzyme or reductant, or after the treatment by reductant further digested by proteolytic enzymes derived from animal, plant and microorganism thereby preparing the bacterial component of Pseudomonas aeruginosa, possessing extremely strong anti-tumor and interferon-inducing activities.

The bacterial component of *Pseudomonas aeruginosa* obtained by the above method possesses an extremely powerful biological activity. As for the method of isolating OEP composed of highly purified protein, further details are given in the description in the British Pat. No. 1,365,950 quoted hereabove.

More concretely, the "powerful biological activity" means anti-tumor and interferon-inducing activities as well as non-specific protection against bacillus and further vaccine activity preventing infection due to Pseudomonas aeruginosa strains regardless of their serotypes.

The present invention aims at the isolation of a bacterial component possessing an extremely powerful biological activity referred to hereabove, the isolation being effected by processing OEP having a powerful biological activity with reductant and digesting it thereafter with proteolytic enzyme.

Using the above method, OEP was obtained by a mass culture of bacterial strains of *Pseudomonas aeruginosa*. This OEP was proved to have a significant biological activity. When expressed in terms of inhibition of the growth of ascites tumor (sarcoma 180), the dose of OEP of 50% inhibition ($ED_{50}$) was 1 μg/kg mouse/day determined according to the method of Kuretani and his associates.

When this OEP is processed by reductants such as sodium borohydride, 2-mercaptoethanol, sodium monothiophosphate and dithiothreitol and fractionated by one of the fractionating methods such as gel filtration, ion exhange resin, salting out by ammonium sulfate and electrophoresis as well as the method using organic solvents such as acetone and ethanol or the combination thereof, a bacterial component possessing a biological property more effective in anti-tumor and interferon-inducing activities can be isolated (refer to Example 1).

As shown in one of the examples, its activity against sarcoma 180A expressed in $ED_{50}$ value was 0.45 μg/kg mouse/day and interferon-inducing activity was 0.01 μg/ml in the concentration representing 18 units. Then, the substance isolated by reductant and possessing a powerful biological activity was digested by proteolytic enzyme. For the above process, proteolytic enzymes derived from aminals, plants and microorganisms are applicable. Suitable enzymes are alkaline protease derived from *Bacillus subtilis*, trypsin and chymotrypsin, and alkaline protease derived from *Pseudomonas aeruginosa*.

A bacterial component possessing the extremely powerful biological activity referred to hereabove can be isolated by one of the conventional fractionating methods such as gel filtration, diaphragm, ion exchange resin, electrophoresis and salting out of ammonium sulfate as well as the method using organic solvents such as acetone and ethanol or the combination thereof after the digesting process has been made by one of or a mixture of these proteolytic enzymes, as will be shown in Examples 2 and 3.

The substance obtained through the treatment by enzyme consists of such components as protein, sugar, aminosugar and lipid whose chemically analyzed values are 15-50%, 10-20%, 10-20%, and 25-40% respectively.

(1) Details on the chemically analyzed values of these substances and chemical properties are given in the relative examples (Examples 1, 2 and 3).

(2) Biological activity (although this activity can be produced by means of injection, it can also be produced by oral administration).

(i) Activity as an antigen (vaccine) possessing specific or non-specific preventive property against infection.

As a non-specific preventive effect actually displayed, mouse infections caused by Klebsiella, Salmonella typhi and Salmonella typhimurium were successfully prevented 24 hours after the mice were immunized with OEP (prior to the treatment by proteolytic enzyme).

Mice were protected against challenges carried out with Fisher's 7 immunotype strains and 14 kinds of Homma's serotype strains shown in Tables A and B.

Table A

Effects of OEP vaccination on protection of mice against challenge with each of the 14 serotype strains of Homma's serotype

| Serotype of strain used to challenge mice | $LD_{50}$ (No. of live bacilli) | | Difference between (A) and (B) |
|---|---|---|---|
| | Immunized (A) | Untreated (B) | |
| T 1 | $2.6 \times 10^4$ | $2.6 \times 10^3$ | S |
| T 2 | $3.2 \times 10^3$ | $2.0 \times 10^1$ | S |
| T 3 | $2.8 \times 10^3$ | $2.8 \times 10^2$ | S |
| T 4 | $>2.0 \times 10^8$ | $2.0 \times 10^7$ | S |
| T 5 | $>2.2 \times 10^7$ | $<2.2 \times 10^1$ | S |
| T 6 | $>1.5 \times 10^8$ | $1.5 \times 10^6$ | S |
| T 7 | $2.4 \times 10^2$ | $2.4 \times 10^1$ | S |
| T 8 | $1.5 \times 10^6$ | $1.5 \times 10^4$ | S |
| T 9 | $3.8 \times 10^4$ | $<3.8 \times 10^2$ | S |
| T 10 | $4.1 \times 10^6$ | $1.0 \times 10^5$ | S |
| T 11 | $1.9 \times 10^3$ | $7.5 \times 10^1$ | S |
| T 12 | $5.3 \times 10^5$ | $<2.1 \times 10^3$ | S |
| T 13 | $3.3 \times 10^4$ | $6.6 \times 10^1$ | S |
| T 14 | $<2.9 \times 10^6$ | $2.9 \times 10^4$ | S |

Mice were immunized by intraperitoneal administration of OEP, and a week after the last injection, each mouse was intraperitoneally injected with 0.5 ml of live bacilli suspended in 2-5% mucin solution.

S: Significant.

TABLE B

Effects of OEP vaccination on protection of mice against challenge with each of 7 kinds of strains of Fisher's immunotypes

| Serotype of strain used to challenge mice | $LD_{50}$ (No. of live bacilli) | | Difference between (A) and (B) |
|---|---|---|---|
| | Immunized (A) | Untreated (B) | |
| F 1 | $1.4 \times 10^7$ | $8.8 \times 10^4$ | S |
| F 2 | $>1.7 \times 10^6$ | $2.1 \times 10^4$ | S |
| F 3 | $>1.4 \times 10^7$ | $5.4 \times 10^3$ | S |
| F 4 | $3.8 \times 10^5$ | $1.5 \times 10^4$ | S |
| F 5 | $>3.9 \times 10^5$ | $1.0 \times 10^4$ | S |
| F 6 | $1.0 \times 10^6$ | $6.3 \times 10^4$ | S |
| F 7 | $>1.4 \times 10^7$ | $1.8 \times 10^3$ | S |

Mice were injected with OEP intraperitoneally, and a week after the last injection, they were challenged intraperitoneally with live bacilli suspended in 0.5 ml of 2-5% mucin solution.

As shown in Example 5, the experimental results on protective immunity conferred by the component which had been treated with proteolytic enzyme and isolated at peak 1, revealed that it could not protect mice from all the serotype strains belonging to Fisher's immunotypes, though the OEP was protective before the treatment with proteolytic enzyme (refer to Table C).

TABLE C

Effects of protease-treated OEP vaccination on protection of mice against challenge with each of 7 kinds of strains of Fisher's immuno- of *Pseudomonas aeruginosa*

| Serotype of strain used to challenge mice | $LD_{50}$ (No. of live bacilli) Immunized (A) | Untreated (B) | Difference between (A) and (B) |
|---|---|---|---|
| F 1 | $1.5 \times 10^4$ | $<3.7 \times 10^2$ | S |
| F 2 | $7.9 \times 10^3$ | $2.0 \times 10^2$ | S |
| F 3 | $2.1 \times 10^2$ | $1.5 \times 10^2$ | NS |
| F 4 | $3.1 \times 10^4$ | $1.9 \times 10^4$ | NS |
| F 5 | $3.7 \times 10^4$ | $<2.4 \times 10^2$ | S |
| F 6 | $3.9 \times 10^5$ | $6.3 \times 10^2$ | S |
| F 7 | $6.5 \times 10^4$ | $4.1 \times 10^2$ | S |

Mice were injected with protease-treated OEP intraperitoneally, and in a week they were challenged intraperitoneally with live bacilli suspended in 0.5 ml of 2.5% mucin solution.

S: Significant
NS: Not significant

Therefore, although a vaccine prepared from protease-treated OEP is not quite as effective as the intact OEP which was not given by the enzyme treatment, it still has a powerful activity to a broad extent as an immunopotentiator in the in vivo protection mechanism.

(ii) Anti-tumor activity:

As for the measurement of anti-tumor activity, the effect on the inhibition of the growth of tumor against mouse ascites tumor (sarcoma 180) was investigated using the method employed by Kuretani et al. (Chem. Pharm. Bull, 17, 848, 1969).

Female mice weighing 18–20 g, ddN, each group divided into 6 mice, were used for the experiment. The method adopted was the intraperitoneal transplantation of 0.05 ml of seven-day-old ascites tumor cells ($1 \times 10^7$) into each mouse; from the next day on, 0.05 ml of a saline solution containing the test sample was intraperitoneally injected into a mouse once daily for 5 days. A specimen of ascites fluid was removed 7 days after the tumor transplantation, and the total cell volume contained therein was expressed as the percentage of the total cell volume of the control groups (groups given physiological saline solution.

When investigated by this method, the OEP before the treatment by proteolytic enzyme proved to be a substance whose dose ($ED_{50}$) required for inhibiting the growth of 50% tumor cells corresponded to 1 μg/kg mouse/day and exhibit almost no deviation due to the difference of lots used for the culture as shown in Table D.

TABLE D

Anti-tumor activity of OEP derived from different lots

| Lot No. | $ED_{50}$ (μg/kg mouse/day) |
|---|---|
| 1 | 1.50 |
| 2 | 1.20 |
| 3 | 0.90 |
| 4 | 1.00 |
| 5 | 0.72 |
| average | $1.06 \pm 0.13$ |

TABLE E

Anti-tumor activities of bacterial components of *Pseudomonas aeruginosa* other than OEP and those of other microorganisms

| Test Solution | $ED_{50}$ (μg/kg/day) |
|---|---|
| Component I*[1] (Pseudomonas aeruginosa P I-III) | 100 |
| Component II*[2] (Pseudomonas aeruginosa P I-III) | 500 |
| Pyocine Rmc*[3] (Pseudomonas aeruginosa P 15) | 1,000 |
| Conjugated protein*[4] (Shigella dysenteriae) | 14 |
| Zymosan*[5] (Saccharomyces cerevisiae) | 700 |

*[1] OEP - LPS conjugate
*[2] Nucleic acid polyribose phosphate conjugate
*[3] Simple protein
*[4] Conjugated protein
*[5] Hydroglucan It was also found out that OEP was a substance possessing an extremely powerful activity when compared with bacterial components derived from other microorganisms and the components other than OEP derived from *Pseudomonas aeruginosa* as shown in Table E. Furthermore, as shown in Examples 1, 2, and 3, it was confirmed that the above $ED_{50}$ value of OEP had increased up to 0.2 μg/kg mouse/day after chemical treatments, and that these anti-tumor activities could also be expected by oral administration.

(iii) Interferon-inducing activity:

The interferon-inducing activity (IF) was measured by the method employed by Kojima et al. ("Interferon", Igakushoin, 74–83, 1970, Kitasato Arch. Exp. Med., 43, 1970, Japan J. Microbiol., 18, 217–222, 1974).

A culture solution containing 0.005% calcium chloride and 10% calf serum was used as the buffer solution of 1/200 mol. 10 fold diluent of the test solution was then prepared, and this test solution was mixed with 1–2 $\times 10^7$ cells of young rabbit (spleen cells or lymphnode cells) weighing 800–1,000g. This mixture was cultivated in a tube at 25° C for 24 hours. As for the centrifuged supernatant, the productivity of interferon-inducing property was determined by use of RK13 cell line of rabbit kidney and Vesicular Stomatitis virus.

Interferon unit (IF value) was expressed by a reciprocal of the dilution multiple of the above culture supernatant required for reducing the Plaque count (approximately 100) of the control group down to 50%. As shown in Examples 1, 2 amd 3 as well as Table F, it was found out that the IF value of OEP could be increased up to a potency of approximately 10 times higher when OEP was treated with enzyme.

TABLE F

| Interferon-inducing (IF) properties | | | |
|---|---|---|---|
| | IF VALUE | | |
| | Sample 1 | Concentration 0.1 | (μg/ml) 0.01 |
| OEP | 450 | 140 | 12 |
| OEP-ME*[1] | 490 | 310 | 18 |
| OEP-ME-Pro*[2] (Hay bacillus) | 470 | 440 | 184 |
| OEP-ME-Pro*[3] (Pseudomonas aeruginosa) | 470 | 310 | 132 |
| OEP-ME-Pep*[4] | 480 | 330 | 202 |

TABLE F-continued

| | Interferon-inducing (IF) properties | | |
|---|---|---|---|
| | | IF VALUE | |
| | Sample 1 | Concentration 0.1 | (μg/ml) 0.01 |
| OEP-ME-Try*5 | 490 | 390 | 214 |

*1 Peak I isolated in Example 1
*2 Peak I isolated in Example 2
*3 Peak I isolated in Example 1 was digested by Protease derived from Pseudomonas aeruginosa and the component was obtained through gel filtration.
*4 Peak I isolated in Example 1 was digested by Pepsin (prepared by Sigma) and the component was obtained through gel filtration.
*5 Peak I isolated in Example 3.

The production of serum interferon was recognized when OEP was intravenously injected into rabbits. The development of vaccina cirus on skin was inhibited by orally administering OEP to rabbits (see Example 4).

EXAMPLE 1

Figure 1:
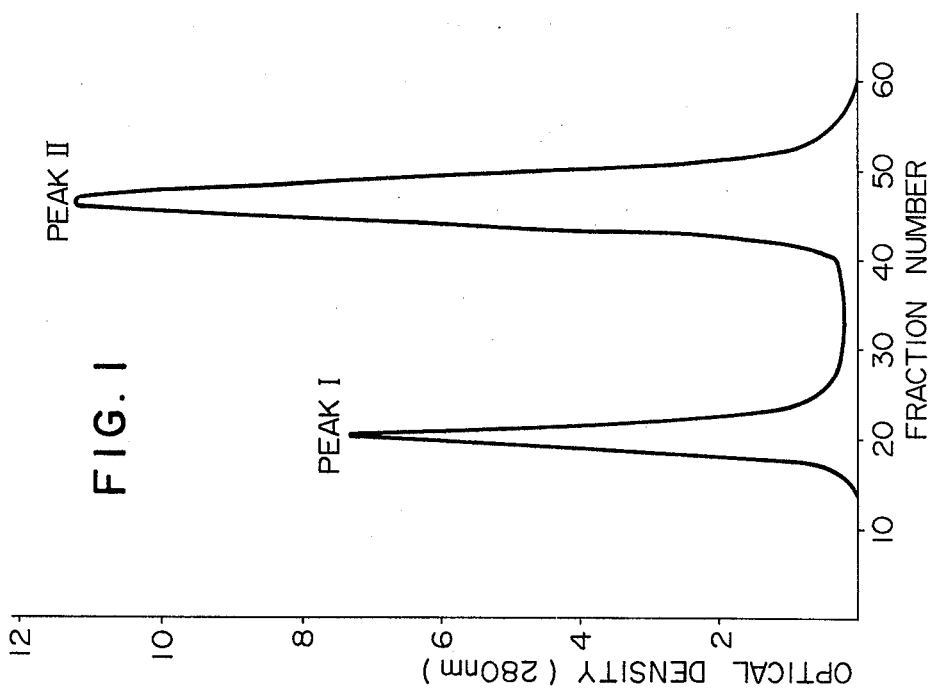
FIG. 1 is a graph showing the elution pattern of 2-mercaptoethanol-treated OEP resulting from a column chromatography on Sephadex G75.

90 mg of OEP was dissolved into a buffer solution of pH 8.0, 2-mercaptoethanol was added so that a 4% solution (volume/volume) was obtained. The solution after reacting at room temperature for 18 hr. ws fractionated by column chromatography on Sephadex G75 equilibrated with the buffer solution in the presence of 4% 2-mercaptoethanol, and then separated into 2 fractions as shown in FIG. 1.

In the fraction at Peak I, 42 mg, dry weight, representing 46% of the original sample was collected and the rest was collected in the fraction isolated at Peak II. An investigation carried out on the activity of these two fractions revealed that $ED_{50}$ at Peak I against ascites tumor (sarcoma 180) was 0.45 μg/kg mouse/day, $ED_{50}$ for the Peak II fraction was more than 30 μg. The IF activity represented 18 units with the concentration of 0.01 μg/ml, while the same at Peak II was higher than 1 μg/ml. As is proved by the above result, most of the active portion of OEP (anti-tumor and IF-inducing activities) could be fractionated out because of the correlation between the activity and yield at Peak I.

When measured by the method moified by Lowry et al., using bovine serum albumin as the standard protein, a substance obtained from a fraction at Peak I possessing a powerful activity contained 77% protein, and when measured by an amino-acid analyzer and expressed in molar ratios, its amino-acid composition was 6.6% lysine, 2.3% histidine, 4.3% arginine, 8.4% aspartic acid, 5.7% threonine, 5.4% serine, 11.7% glutamic acid, 4.6% proline, 8.3% glycine, 11.6% alanine, 7.3% valine, 2.1% methionine, 4.8% isoleucine, 8.9% leucine, 2.8% tyrosine, 3.9% phenylalanine, 1.2% tryptophan, and 1.2% cystine.

The sugar content was found to be 4.5% glucose when measured by a method using anthrone reagent, and the measurement made by gas chromatography revealed that the sugar was composed of 13.9% rhamnose, 4.2% mannose and 61.8% glucose, the rest of the composition being unidentified.

The amino-acid content was 4.5% when measured by the Elson-Morgan method for which glucosamine was used as the standard sample. 2-keto-3-deoxyoctonate (KDO) was 1.3% when determined by the method using thiobarbiturate, and phosphorus was 1.2% by Allen's method. As the result of chemical analyses, lipid was proved to be 8.8%, while the composition of fatty acid as determined by gas chromatography was as follows:

C16:0 43.5%; C16:1 5.8%; C18:0 4.8%; C18:1 22.2%.

An electro-focussing method had revealed an isoelectric point of this substance at pH 4.35 and the maximum absorption in its ultraviolet region at 278 nm.

EXAMPLE 2

20 mg of the substance at Peak I in Example 1 which possessed a powerful activity was dissolved in a buffer solution of pH 8.0. To this solution 1 mg (5% weight/weight) of alkaline protease derived from B. subtilis (Nagase Sangyo K.K. in Japan) was added and kept at 37° C for 18 hours.

Then the mixture was subjected to column chromatography on Sephadex 75 and was separated into 3 fractions (elution pattern by column chromatography is shown in FIG. 2). An investigation carried out on the activities of these 3 fractions revealed that $ED_{50}$ at Peak I was 0.2 μg/kg mouse/day against sercoma 180A and the same at Peak II and III was more than 10 μg.

On the other hand, the interferon-inducing activity was shown in the concentration of 0.01 μg/ml with 184 units at Peak I and 10 μg/ml with 45 units at Peak II and no activity was exhibited at lower concentrations. In other words, a substance possessing an extremely powerful activity was fractioned at Peak I. When measured by the method employed for Example 1, the chemical composition of this substance fractionated at Peak I was 17% protein, 14.5% sugar, 12.5% aminosugar, 3.8% KDO, 2.7% P and 31% lipid, and the compositions of both sugar and fatty acid were the same as those shown in Example 1.

EXAMPLE 3

20 mg of the substance at Peak I in Example 1 which possessed a powerful activity was dissolved in a buffer solution of pH 7.8. To this solution 1 mg of trypsin (Sigma Co.) was added and the solution was kept at 37° C for 18 hours, and then fractionated by column chromatography on Sephadex G75 thereby obtained 3 fractions just as in Example 2. 8 mg (dry weight) of the substance was collected from the fraction which was first eluted. When the activity was investigated, the fraction at Peak I showed 0.25 μg/kg mouse/day against sarcoma 180A and interferon-inducing activity showed the concentration of 0.01 μg/ml with 214 units. A bacterial component with a powerful activity was thus isolated at Peak I. It was also found out that the substance fractionated at this Peak I contained 47% protein.

EXAMPLE 4

OEP was orally administered to young rabbits weighing 600-900 g for a total of 7 times in a single dose of 1 mg/kg 6, 4, 2 and 0 days and 1, 3 and 5 days, respectively, before and after the challenges were made against virus. On the day OEP was administered, 0.1 ml of various dilutions of virus solution was given to the rabbits intracutaneously. Determination was made 7 days after the challenge against virus was carried out, and vaccine lesion in rabbit skin was successfully inhibited by the component as shown in Table G.

TABLE G

Effects of orally administered OEP in inhibiting the crisis against challenge by vaccinia virus

| No. of rabbit | | Size of lesion Virus Dilution | | | |
|---|---|---|---|---|---|
| | | $10^{-5}$ | $10^{-6}$ | $10^{-7}$ | $10^{-8}$ |
| OEP group | 1 | (−)* | 11 × 11** | (−) | (−) |
| | | | 6 × 6 | (−) | (−) |
| | 2 | (−) | (−) | 12 × 12 | (−) |
| | | | (−) | (−) | (−) |
| | 3 | | 19 × 22 | 19 × 21 | (−) |
| | | | 18 × 18 | 12 × 12 | (−) |
| Control group | | | 10 × 11 | (−) | (−) |
| | | | 18 × 20 | 18 × 18 | (−) |
| | 4 | | 17 × 20 | 12 × 12 | (−) |
| | | | 20 × 20 | (−) | (−) |

* (−) Virus infection inhibited
** Figures indicate the length and width of the lesion (mm).

EXAMPLE 5

Mice divided into groups of 5 were used. The fraction isolated at Peak I described in Example 2 was used for immunization by intraperitoneal administration twice a week for 3 weeks. A week after the final day of injection, live bacilli of each of 7 immunotype strains of Fisher et al. were suspended in a sterile solution, and the suspension was used for the intraperitoneal challenge. After the challenge was carried out, the mice were observed for 1 week, and a significant difference in the mortality between immunized and non-immunized groups was determined by probit analysis diagrammatic method. As shown in Table C, mice immunized with the fraction isolated at Peak I in Example 2, were protected against challenge with 5 out of 7 Fisher's immunotypes.

The amino acid composition mol fraction in % before and after the treatment with proteolytic enzyme, is as follows:

| | Before the treatment with proteolytic enzyme | After the treatment with proteolytic enzyme |
|---|---|---|
| Lys | 3.48 | 4.10 |
| His | 2.28 | 2.52 |
| $NH_3$ | 9.35 | 6.43 |
| Arg | 5.32 | 5.83 |
| $CysO_3H$ | 0.10 | ND |
| Asp | 6.93 | 6.19 |
| Thr | 4.56 | 3.44 |
| Ser | 4.22 | 3.06 |
| Glu | 10.68 | 5.59 |
| Pro | 4.42 | 2.71 |
| Gly | 8.59 | 6.82 |
| Ala | 10.74 | 19.96 |
| Val | 7.36 | 4.87 |
| Met | 1.14 | 0.39 |
| Lleu | 5.16 | 4.17 |
| Leu | 8.33 | 5.75 |
| Tyr | 2.92 | 6.83 |
| Phe | 4.29 | 11.32 |
| Try | 0.12 | ND |

ND: Not determined.

Chemical analyses of OEP before and after protease digestion (Alkaline protease, opt pH 8, *B. subtilis*) are as follows:

| | Before digestion | After digestion |
|---|---|---|
| Total sugars | 4.5% | 14.5% |
| Folin-ciocalteu protein | 77 | 17 |
| Lipid | 8.8 | 31 |
| Hexosamine | 4.5 | 12.5 |
| KDO | 1.3 | 3.8 |
| P | 1.2 | 2.7 |

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language, might be said to fall therebetween.

What is claimed is:

1. A method of preparing bacterial component of *Pseudomonas aeruginosa*, comprising the steps of:
    culturing a strain of *Pseudomonas aeruginosa* at temperature of 37° C in liquid medium and treating same with an autolyzing agent to obtain autolysate,
    isolating bacterial component from said autolysate by means of a suitable physicochemical procedure,
    said bacterial component being original endotoxin protein component mainly consisting of protein, sugar and lipid, and treating said original endotoxin protein component with an effective amount of 2-mercaptoethanol to yield a product of having biological activity substantially greater than that of said original endotoxin protein component,
    said original endotoxin protein component possessing anti-tumor activity, interferon-inducing activity, and non-specific and specific protective properties against infection due to *Pseudomonas aeruginosa* as well as to other bacterial strains.

2. A method as claimed in claim 1, wherein said bacterial component is an original endotoxin protein component containing about 77% of protein, about 4.5% of sugar and about 8.8% of lipid.

3. A method as claimed in claim 1, including the step of processing said product of said treatment with 2-mercaptoethanol with proteolytic enzyme to increase the biological activity of said original endotoxin protein component.

4. The method as defined in claim 1 wherein said step of treating with 2 mercaptoethanol comprises the sub-steps of dissolving said autolysate in a buffer solution at a pH of about 8.0, adding enough 2-mercaptoethanol to said solution to constitute about 4% by volume of the resulting solution, allowing said solution to stand until reaction between the constituents thereof is essentially complete, passing said solution through a chromatographic column containing Sephadex G75 previously equilibrated with said buffer solution containing 4 volume percent of said 2-mercaptoethanol, and isolating the first fraction issuing from said column.

5. The method as defined in claim 4, wherein said first fraction is further digested by protease derived from Pseudomonas aeruginosa and then subjected to gel filtration.

6. The method as defined in claim 4, wherein said first fraction is digested by pepsin and then subjected to gel filtration.

7. A method as claimed in claim 1, wherein said strain is a dissociant strain.

8. A method as claimed in claim 1, wherein said strain is a variant strain.

9. A method as claimed in claim 1, wherein said physicochemical procedure is electrophoresis.

10. A method as claimed in claim 1, wherein said physicochemical procedure is gel filtration.

11. A method as claimed in claim 1, wherein said physicochemical procedure is ion-exchange.

12. A method as claimed in claim 3, wherein said proteolytic enzyme is selected from the group consisting of alkaline protease from *Bacillus subtilis*, from *Pseudomonas aeruginosa*, trypsin and chymotrypsin.

13. The product resulting from the method of claim 1.

14. The product resulting from the method of claim 3.

15. The product resulting from the method of claim 12.

16. A method of preparing bacterial component of *Pseudomonas aeruginosa*, comprising the steps of:
  culturing a strain of *Pseudomonas aeruginosa* at a temperature of 37° C in liquid medium and treating same with an autolyzing agent to obtain autolysate,
  isolating bacterial component from said autolysate by means of a suitable physicochemical procedure,
  said bacterial component being original endotoxin protein component mainly consisting of protein, sugar and lipid, and
  said original endotoxin protein component possessing anti-tumor activity, interferon-inducing activity, and non-specific and specific protective properties against infection due to *Pseudomonas aeruginosa* as well as to other bacterial strains, and
  treating said original endotoxin protein component with proteolytic enzyme to increase the biological activity of said original endotoxin protein component.

17. A method as claimed in claim 3, wherein said processed original endotoxin protein component contains 17% of protein, 31% of lipid, 14% of sugar, 12% of aminosugar, and possesses specific anti-tumor and interferon-inducing activities up to approximately 5 to 10 times higher than prior to treatment with reductant.

18. A method as claimed in claim 3, wherein said processed original endotoxin protein component contains 17% of protein, 31% of lipid, 14% of sugar, 12% of aminosugar, 3.8% of ketodeoxyoctonate, 2.7% of phosphorus, and possesses specific anti-tumor and interferon-inducing activities up to approximately 5 and 10 times higher than (prior) subsequent to treatment with reductant.

* * * * *